United States Patent
Lacy et al.

(10) Patent No.: US 9,810,635 B2
(45) Date of Patent: Nov. 7, 2017

(54) METHOD OF ACCURATE THICKNESS MEASUREMENT OF BORON CARBIDE COATING ON COPPER FOIL

(71) Applicant: Proportional Technologies, Inc., Houston, TX (US)

(72) Inventors: Jeffrey L. Lacy, Houston, TX (US); Murari Regmi, Houston, TX (US)

(73) Assignee: Proportional Technologies, Inc., Houston, TX (US)

( * ) Notice: Subject to any disclaimer, the term of this patent is extended or adjusted under 35 U.S.C. 154(b) by 0 days.

(21) Appl. No.: 14/938,903

(22) Filed: Nov. 12, 2015

(65) Prior Publication Data
US 2016/0161416 A1   Jun. 9, 2016

Related U.S. Application Data

(60) Provisional application No. 62/078,674, filed on Nov. 12, 2014.

(51) Int. Cl.
*G01N 21/00* (2006.01)
*G01N 21/73* (2006.01)
(Continued)

(52) U.S. Cl.
CPC ............. *G01N 21/73* (2013.01); *G01N 21/68* (2013.01); *G01N 2021/8427* (2013.01)

(58) Field of Classification Search
CPC ... B23K 31/027; C23C 14/021; C23C 14/025; C23C 14/0635; G01N 2021/8427;
(Continued)

(56) References Cited

U.S. PATENT DOCUMENTS

| 4,446,173 A | * | 5/1984 | Barrell | ............... | B29C 70/50 |
|   |   |   |   |   | 427/206 |
| 5,751,416 A | * | 5/1998 | Singh | ............... | G01J 3/30 |
|   |   |   |   |   | 356/300 |

(Continued)

FOREIGN PATENT DOCUMENTS

WO   WO 2014/120295 A2 * 8/2014

OTHER PUBLICATIONS (ASTM B504) Standard Test method for measurement of Thickness of Thickness of Metallic Coatings by the Coulometric Method. 2011, sections 1, 3, 6; appendix X1.*

(Continued)

*Primary Examiner* — Hoa Pham
(74) *Attorney, Agent, or Firm* — Hasley Scarano, L.L.P.

(57) ABSTRACT

A method is disclosed of measuring the thickness of a thin coating on a substrate comprising dissolving the coating and substrate in a reagent and using the post-dissolution concentration of the coating in the reagent to calculate an effective thickness of the coating. The preferred method includes measuring non-conducting films on flexible and rough substrates, but other kinds of thin films can be measure by matching a reliable film-substrate dissolution technique. One preferred method includes determining the thickness of Boron Carbide films deposited on copper foil. The preferred method uses a standard technique known as inductively coupled plasma optical emission spectroscopy (ICPOES) to measure boron concentration in a liquid sample prepared by dissolving boron carbide films and the Copper substrates, preferably using a chemical etch known as ceric ammonium nitrate (CAN). Measured boron concentration values can then be calculated.

14 Claims, 4 Drawing Sheets

(51) Int. Cl.
*G01N 21/68* (2006.01)
*G01N 21/84* (2006.01)

(58) Field of Classification Search
CPC . G01B 11/0616; G01B 11/06; G01B 11/0683; G01B 21/08; G01B 15/02; G01B 7/06; G01B 7/066
USPC .......... 356/630–632, 318, 432–440
See application file for complete search history.

(56) References Cited

U.S. PATENT DOCUMENTS

| | | | | |
|---|---|---|---|---|
| 6,827,871 B2* | 12/2004 | Westmoreland | ...... | C22B 11/046 216/100 |
| 2003/0016353 A1* | 1/2003 | Detalle | ................ | B23K 26/032 356/318 |
| 2006/0119867 A1* | 6/2006 | Choi | ................... | G01B 11/0625 356/632 |
| 2007/0296967 A1* | 12/2007 | Gupta | ................... | G01J 3/2889 356/318 |
| 2014/0110247 A1* | 4/2014 | Lacy | ................... | B21C 37/0818 204/192.15 |

OTHER PUBLICATIONS (Fischer, H) Traceability of the amount of Phosphorus in NiP-coatings. Fischer Traceability Report. 2011; sections 1, 2, 5; p. 2, table.*

(Gems Water With IAEA) Analytical Methods for Emvironmental Water Quality. 2004; appendix 2; p. 13 and 134.*

(Menard, G et al.) Precise and accurate determination of boron concentration in silicate rocks by direct isotope dilution ICP-MS: Insights into the B budget of the mantle and B behavior in magmatic systems. Chemical Geology. Jun. 26, 2013. vol. 354; p. 141, section 2.1.*

* cited by examiner

METHOD OF ACCURATE THICKNESS MEASUREMENT OF BORON CARBIDE COATING ON COPPER FOIL

RELATED APPLICATIONS

This application claims priority to U.S. Provisional Application No. 62/078,674 ("the '674 Application") filed Nov. 12, 2014. The '674 Application is hereby incorporated by reference in its entirety for all purposes, including but not limited to, all portions describing the measurement process of the present invention, those portions describing boron-coated straw detectors in general as background and for use with specific embodiments of the present invention, and those portions describing other aspects of manufacturing and testing of boron-coated straws that may relate to the present invention.

GOVERNMENTAL SPONSORSHIP

This invention was made with support under DE-SC0009615 awarded by the Department of Energy. The government may have certain rights in the invention.

REFERENCE TO A SEQUENTIAL LISTING

Not applicable.

BACKGROUND OF THE INVENTION

Field of the Invention

This invention relates to measuring coatings or films on substrates. More particularly, this invention relates to measuring boron carbide coatings on thin metallic foils.

Description of the Related Art

A number of different techniques are in use to measure thin film thickness including optical or x-ray interferometry, surface profilometry, scanning probe microscopy, cross section electron microscopy and others. Each of these techniques has their own advantages and disadvantages. For example optical or x-ray interferometry can be used to measure wide range of thicknesses ranging from nanometers to several micrometer but requires extremely smooth and flat film-substrate interface. This technique becomes unusable when it comes to a substrate having flexible or rough surface or both. Surface profilometry requires a sharp step height and rigid sample surface. Scanning probe microscopy can measure just few nanometers height and requires a sharp step height and smooth surface. One of the techniques very widely used is the electron microscopy including both scanning electron microscopy (SEM) and transmission electron microscopy (TEM). SEM can be used to measure in a wide range from tens of nanometers to millimeters and TEM can be used to accurately measure thickness in nanometer scale. However, both of these techniques are very local and require huge effort in sample preparation and can take several hours to measure one sample. It becomes even more difficult when it comes to non-conducting ceramic films since an additional conducting coating is required. Sample preparation becomes even more tedious when the substrate is flexible. Since the techniques are very local measured value will have very high uncertainty for films with rough surface.

Boron-coated straw detector technology was first patented by Dr. Lacy in U.S. Pat. No. 7,002,159 entitled "Boron-Coated Straw Neutron Detector" based upon a Nov. 13, 2002, filing. As the thought leader of this technology area, Dr. Lacy continued his research and development to improve the boron coated straw detectors technology and to find new uses. Examples of Dr. Lacy's continued progress in this technology area are found in his other issued patents and pending patent applications which include: U.S. Pat. No. 8,330,116 entitled "Long Range Neutron-Gamma Point Source Detection and imaging Using Rotating Detector"; U.S. Pat. No. 8,569,710 entitled "Optimized Detection of Fission Neutrons Using Boron-Coated Straw Detectors Distributed in Moderator Material"; U.S. Pat. No. 8,907,293, entitled "Optimized Detection of Fission Neutrons Using Boron-Coated Straw Detectors Distributed in Moderator Material"; U.S. patent application Ser. No. 13/106,785 filed May 12, 2011, entitled "Sealed Boron-Coated Straw Detectors" (allowed and issue fee paid); U.S. patent application Ser. No. 13/106,818 filed May 12, 2011, entitled "Neutron Detectors for Active Interrogation" (allowed and issue fee paid); U.S. Pat. No. 8,941,075, entitled "Boron Coated Straw Detectors with Shaped Straws"; U.S. application Ser. No. 14/060,015 filed Oct. 22, 2013, entitled "Method and Apparatus for Coating Thin Foil with a Boron Coating"; and U.S. application Ser. No. 14/060,507 filed Oct. 22, 2013, entitled "Method and Apparatus for Fabrication Boron Coated Straws for Neutron Detectors." The patent and pending applications mentioned in this paragraph are hereby incorporated by reference in their entirety for all purposes, including but not limited to those portions describing the structure and technical details of the boron-coated straw detectors and boron coating as background and for use as specific embodiments of the present invention, and those portions describing other aspects of manufacturing and testing of boron-coated straws that may relate to the present invention.

Dr. Lacy also widely published articles on boron-coated straw detection capabilities, fabrication, and development of prototypes for various applications including:

J. L. Lacy, et al, "Novel neutron detector for high rate imaging applications", *IEEE Nuclear Science Symposium Conference Record*, 2002, vol. 1, pp. 392-396;

J. L. Lacy, et al, "Straw detector for high rate, high resolution neutron imaging", in *IEEE Nuclear Science Symposium Conference Record*, 2005, vol. 2, pp. 623-627;

J. L. Lacy, et al, "High sensitivity portable neutron detector for fissile materials detection", *IEEE Nuclear Science Symposium Conference Record*, 2005, vol. 2, pp. 1009-1013;

J. L. Lacy, et al, "Performance of 1 Meter Straw Detector for High Rate Neutron Imaging", *IEEE Nuclear Science Symposium Conference Record*, 2006, vol. 1, pp. 20-26;

J. L. Lacy, et al, "Long range neutron-gamma point source detection and imaging using unique rotating detector", *IEEE Nuclear Science Symposium Conference Record*, 2007, vol. 1, pp. 185-191;

J. L. Lacy, et al, "Fabrication and materials for a long range neutron-gamma monitor using straw detectors", *IEEE Nuclear Science Symposium Conference Record*, 2008, pp. 686-691;

J. L. Lacy, et al, "One meter square high rate neutron imaging panel based on boron straws", *IEEE Nuclear Science Symposium Conference Record*, 2009, pp. 1117-1121;

J. L. Lacy, et al, "Boron coated straw detectors as a replacement for $^3$He", *IEEE Nuclear Science Symposium Conference Record*, 2009, pp. 119-125;

J. L. Lacy, et al, "One meter square high rate neutron imaging panel based on boron straws", *IEEE* 2009 *Nuclear Science Symposium Conference Record*, 2009, pp. 1117-1121;

J. L. Lacy, et al, "Initial performance of large area neutron imager based on boron coated straws", *IEEE* 2010 *Nuclear Science Symposium Conference Record*, 2010, pp. 1786-1799;

J. L. Lacy, et al, "Initial performance of sealed straw modules for large area neutron science detectors", *IEEE* 2011 *Nuclear Science Symposium Conference Record*, 2011, pp. 431-435;

J. L. Lacy, et al, "Straw-Based Portal Monitor $^3$He Replacement Detector with Expanded Capability", *IEEE* 2011 *Nuclear Science Symposium Conference Record*, 2011, pp. 431-435;

J. L. Lacy, et al, "Performance of a Straw-Based Portable Neutron Coincidence/Multiplicity Counter", *IEEE* 2011 *Nuclear Science Symposium Conference Record*, 2011, pp. 529-532;

J. L. Lacy, et al, "Replacement of $^3$He in Constrained-Volume Homeland Security Detectors", *IEEE* 2011 *Nuclear Science Symposium Conference Record*, 2011, pp. 324-325;

J. L. Lacy, et al, "Initial performance of sealed straw modules for large area neutron science detectors", *IEEE* 2011 *Nuclear Science Symposium Conference Record*, 2011, pp. 431-435;

J. L. Lacy, et al, "Boron-coated straws as a replacement for 3He-based neutron detectors", *Nuclear Instruments and Methods in Physics Research*, Vol. 652, 2011, pp. 359-363;

J. L. Lacy, et al, "Design and Performance of High-Efficiency Counters Based on Boron-Lined Straw Detectors", *Institute of Nuclear Materials Management Annual Proceedings*, 2012;

J. L. Lacy, et al, "Boron-coated straw detectors of backpack monitors", *IEEE Transactions on Nuclear Science*, Vol. 60, No. 2, 2013, pp. 1111-1117.

J. L. Lacy, et al, "The Evolution of Neutron Straw Detector Applications in Homeland Security", *IEEE Transactions on Nuclear Science*, Vol. 60, No. 2, 2013, pp. 1140-1146.

The publications mentioned in this paragraph are hereby incorporated by reference in their entirety for all purposes, including but not limited to those portions describing the structure and technical details of the boron-coated straw detectors and boron coatings as background and for use as specific embodiments of the present invention, and those portions describing other aspects of manufacturing and testing of boron-coated straws that may relate to the present invention.

SUMMARY OF THE INVENTION

This present invention is a method of measuring the thickness of a thin coating on a substrate comprising dissolving the coating and substrate in a reagent and using the post-dissolution concentration of the coating in the reagent to calculate an effective thickness of the coating. The preferred method is especially useful for non-conducting films on flexible and rough substrates, even though it is equally useful for other kinds of thin films provided a reliable film-substrate dissolution technique is found. A preferred method includes determining the thickness of Boron Carbide films deposited on copper foil (for example 25 um thick flexible cold rolled Copper foil). Effective thickness of the boron carbide thin film can be defined as the thickness of a pure boron carbide film which contains the same numbers of boron atoms as in the real boron carbide film. For a film with quite rough surface like that of boron carbide on Cu foil, very locally measured thicknesses has very little significance and can be easily misleading, rather an average thickness from a large region can accurately provide the number of atoms of interest within the sample. The preferred method uses a standard technique known as inductively coupled plasma optical emission spectroscopy (ICPOES) to measure boron concentration in a liquid sample prepared by dissolving boron carbide films and the Copper substrates, preferably using a chemical etch known as ceric ammonium nitrate (CAN). Measured boron concentration values can be converted to effective thickness ($t_{eff}$) using the equations shown below.

Additional advantages of the invention are set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF SEVERAL VIEWS OF THE DRAWINGS

A better understanding of the invention can be obtained when the detailed description set forth below is reviewed in conjunction with the accompanying drawings, in which.

DETAILED DESCRIPTION OF VARIOUS EMBODIMENTS OF THE INVENTION

This present invention is a method of measuring the thickness of a thin coating on a substrate comprising dissolving the coating and substrate in a reagent and using the post-dissolution concentration of the coating in the reagent to calculate an effective thickness of the coating. The preferred method is especially useful for non-conducting films on flexible and rough substrates, even though it is equally useful for other kinds of thin films provided a reliable film-substrate dissolution technique is found. A preferred method includes determining the thickness of Boron Carbide films deposited on copper foil (for example 25 um thick flexible cold rolled Copper foil). Effective thickness of the boron carbide thin film can be defined as the thickness of a pure boron carbide film which contains the same numbers of boron atoms as in the real boron carbide film. For a film with quite rough surface like that of boron carbide on Cu foil, very locally measured thicknesses has very little significance and can be easily misleading, rather an average thickness from a large region can accurately provide the number of atoms of interest within the sample. The preferred method uses a standard technique known as inductively coupled plasma optical emission spectroscopy (ICPOES) to measure boron concentration in a liquid sample prepared by dissolving boron carbide films and the Copper substrates, preferably using a chemical etch known as ceric ammonium nitrate (CAN). Measured boron concentration values can be converted to effective thickness ($t_{eff}$) using the equations shown below.

Figure 1:
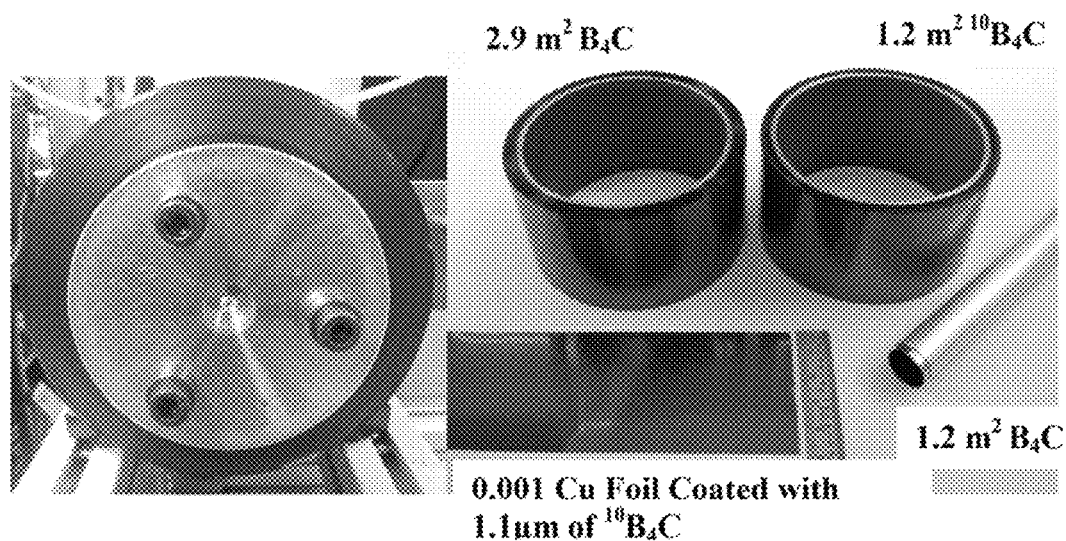
FIG. 1 depicts examples of reels of copper foil coated with boron carbide such as are known in the art.

Copper foil can be coated with boron carbide (10B4C) using a number of methods including the process disclosed in Applicant's pending application, U.S. application Ser. No. 14/060,015. FIG. 1 shows examples of reels of Copper foils coated with boron carbide. This coated product is used in fabricating neutron detectors for different purposes as described in our previous patents and publications.

Easy and reliable measurement of the boron carbide film thicknesses at different locations in the reel is extremely important to assess the coating thickness uniformity.

Figure 2:
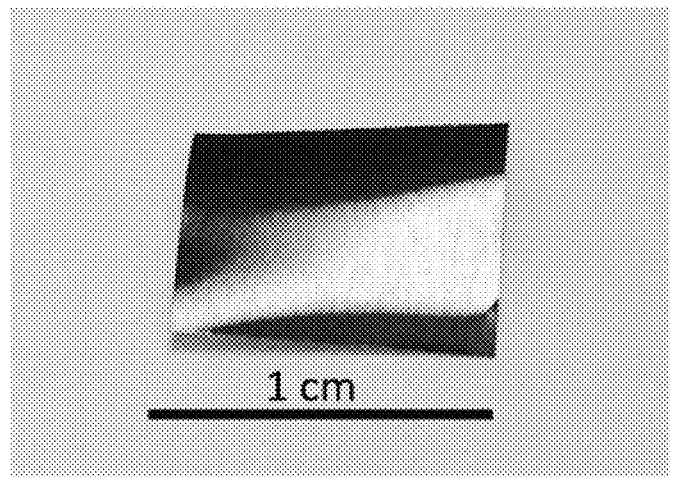
FIG. 2 depiction a boron carbide coated sample such as may be utilized in a preferred method.

In one embodiment of the method of the present invention, samples of coated coil as shown in FIG. 2 is taken from a various locations and accurately weighed, preferably up to four decimal places, in grams. Preferably, the method is used for measuring average effective thickness of boron carbide films from samples of larger than 1 cm$^2$ in size. Preferably, a sample size is at least about 1 cm by 1 cm. Preferably, such samples are taken every 50 to 200 feet of foil.

Figure 3:
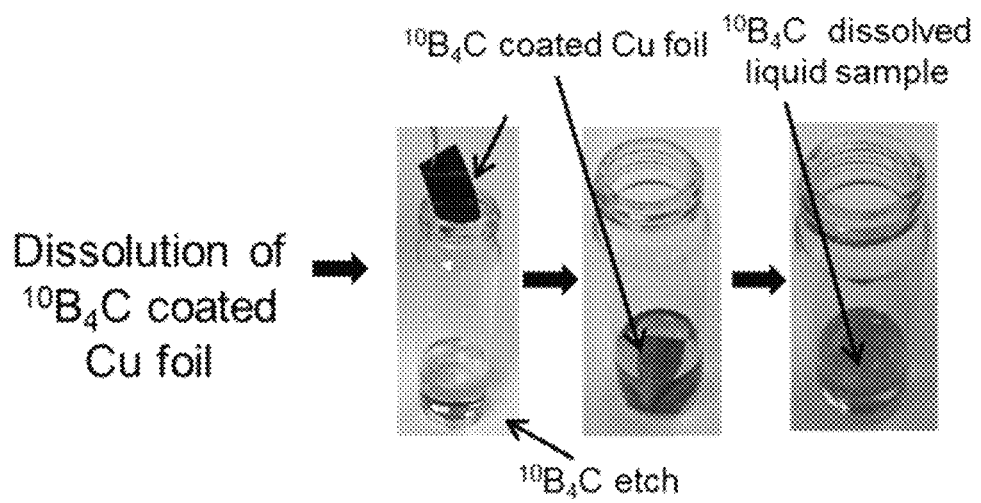
FIG. 3 depicts the dissolution of boron carbide and Cu foil using ceric ammonium nitrate such as may be accomplished using a preferred method of the invention.

As shown in FIG. 3, the next step in a preferred embodiment of the method of the present invention involves dissolving the coating samples in CAN solution at ambient conditions. Standard ceric ammonium nitrate solution is commercially available or it can be locally prepared with a desired concentration from ceric ammonium nitrate powder dissolved in DI water. As can be seen in FIG. 3, the CAN is a yellowish solution prior to addition of the sample (Stage 1). During the dissolution process (Stage 2), the solution turns a brownish color and ultimately a greenish color indicating complete dissolution (Stage 3). No gas is evolved during the dissolution process so that the samples can be dissolved in a closed container. The concentration of CAN can be varied to optimize the dissolution time. Preferably, the concentration of CAN is in the range of 2.5 to 20%, and more preferably in the range of 8 to 10%.

Figure 4:
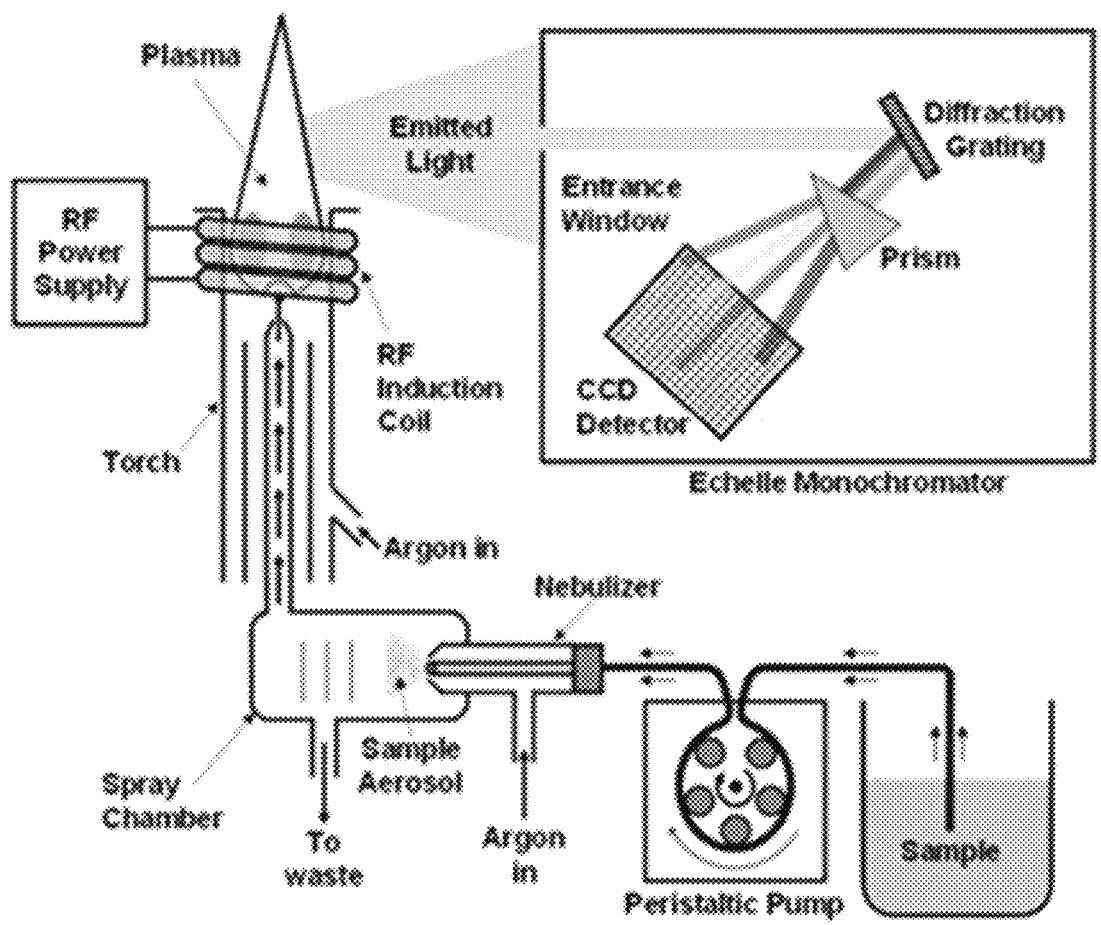
FIG. 4 depicts a standard ICPOES measurement set up such as may be utilized in a preferred method of the invention for boron concentration measurement from the liquid samples.

Prepared solution is appropriately diluted to prepare the final measurement solution so that the reduced boron concentration value lies within the appropriate range for the ICPOES equipment. Preferably, the final boron concentration is reduced down to about 2-25 PPM. If the concentration is too high the optical detector can get saturated. When an external liquid sample is sent through a plasma (See FIG. 4), the constituent atoms of the sample are excited and optical emission is occurred when the previously excited atoms are de-excited. Intensities for a given emission wavelength increases linearly with the concentrations. Emitted wavelength's positions and intensities from the unknown sample are compared with a calibration straight line derived using standards with different concentrations and a given standard to measure the concentration from the unknown samples.

Figure 5:
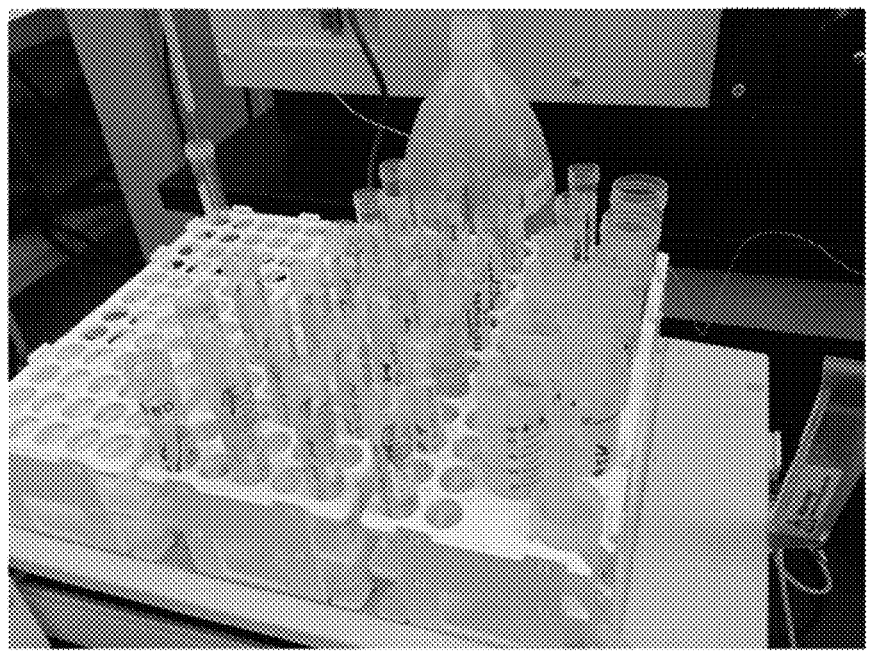
FIG. 5 depicts an example of the preferred method of the invention in which more than 10 samples are utilized on ICPOES stage for boron concentration measurement.

As shown in FIG. 5, several liquid samples can be prepared and set up on ICPOES stage for boron concentration measurement at the same time. This method is quite fast such that several samples (more than 20) can be measured in just few hours. Preferably, using this embodiment of the preferred method, boron concentration can be easily measured to ¹/₁₀th of PPM concentration so that this method is also extremely accurate.

Once the concentrations have been determined using, the next step of the preferred method is to calculate an effective thickness of the boron coating. Preferably, the effective thickness is calculated using the following equations:

Assuming Mt as the total mass of the sample taken, sum of the mass of Copper foil ($M_{cu}$) and mass of the boron carbide film ($M_s$), area of the sample surface (A) can be given by following equation:

$$A = M_t / (t_s \times d_s + t_{cu} \times d_{cu}) \quad (1)$$

Where, $t_s$ = effective thickness of boron carbide film
$d_s$ = density of boron carbide
$t_{cu}$ = thickness of Cu foil
$d_{cu}$ = density of Cu foil.

The equation for the area of the sample face can be used to compute the effective thickness of the boron carbide film using the following equation.

$$t_s = [(1.3 \times C \times V_s \times d_f \times t_{cu} \times d_{cu} / M_t) \times 1/(1 - 1.3 \times C \times V_s \times d_f / M_t)] \quad (2)$$

Where, C = measured boron concentration using ICPOES
$d_f$ = sample dilution factor
$V_s$ = Volume of the liquid sample prepared For calculation of the effective film thickness, density of the boron carbide film can be assumed to be same as the bulk density of boron carbide. In pure boron carbide, 4 boron atoms are attached with one carbon atoms so that the effective boron carbide concentration is given by 1.3 times the measured boron concentration by ICPOES.

Figure 6:
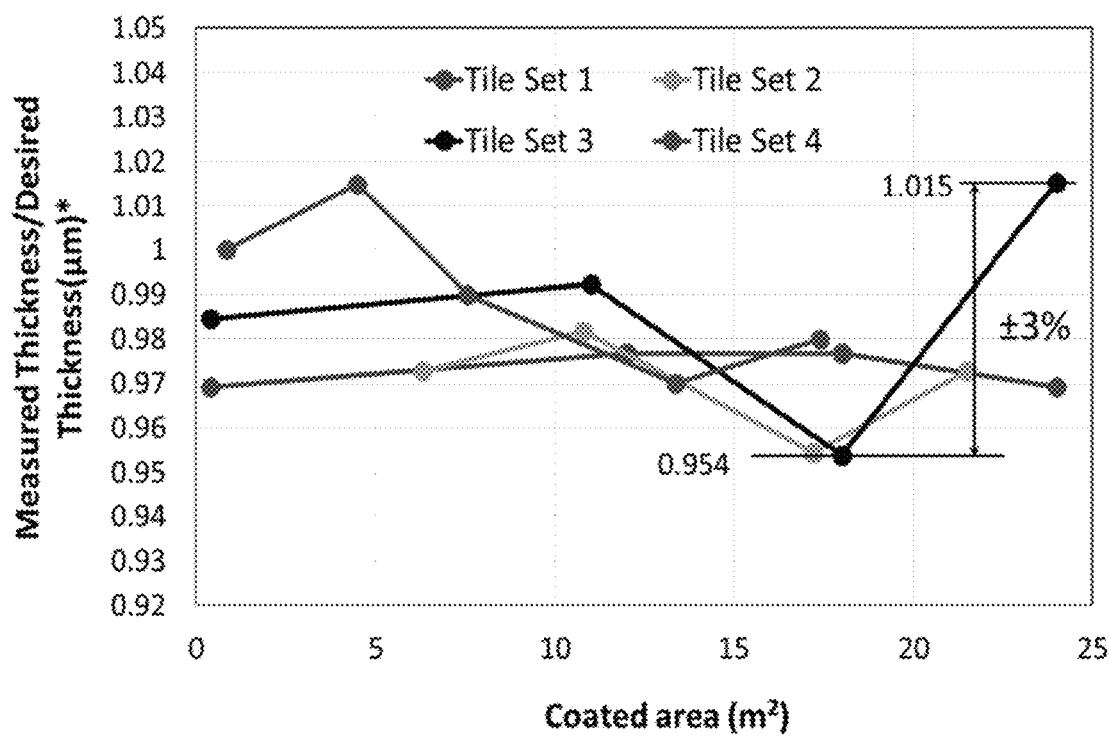
FIG. 6 is plot showing the ratio of effective thickness to desired thickness of boron carbide coating results from tests using a preferred embodiment of the method of the invention for four different sputtering boron carbide tile sets on standard 25 μm thick Copper foil.
Figure 7:
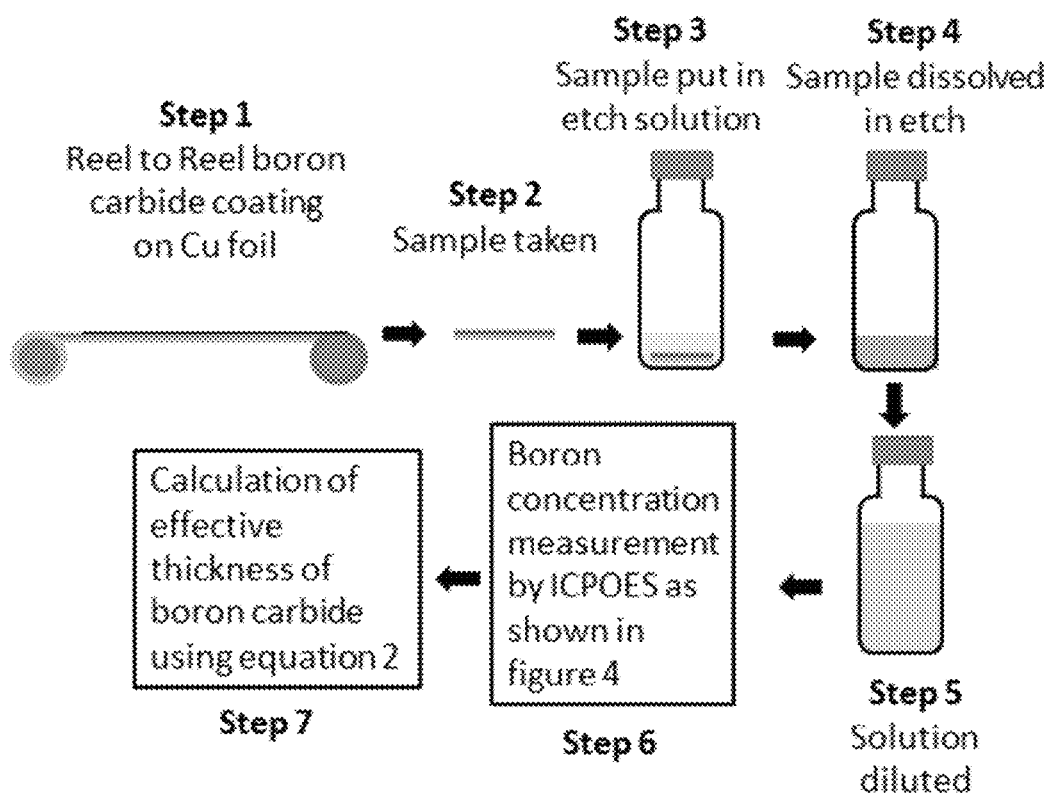
FIG. 7 is a process flow diagram of steps of a preferred version of the method of the present invention.

Using this preferred embodiment of the method several samples taken from different locations of coated product were taken and the effective thickness was measured from the product from several sputtering boron carbide tiles. Results taken from four different tiles are shown in FIG. 6. The measurements indicate a uniform thickness within +/−3% for the entire coated area of the boron-coated tiles. Some of the results were also compared with SEM measurements and were found in very good agreement to each other. The parameters utilized for this testing are as follows:

| $M_t$ (gm) | $t_{cu}$ (μm) | $d_{cu}$ (gm/cc) | $V_s$ (ml) | $d_f$ | $d_s$ (gm/cc) | C (mg/l) | $t_s$ (μm) |
|---|---|---|---|---|---|---|---|
| 0.05-0.12 | 25 | 8.96 | 10-20 | 20-30 | 2.38 | 3-10 | 1-2 |

While the terms used herein are believed to be well-understood by one of ordinary skill in the art, definitions are set forth to facilitate explanation of certain of the presently-disclosed subject matter.

Following long-standing patent law convention, the terms "a", "an", and "the" refer to one or more when used in this application, including the claims. Thus, for example, reference to "a window" includes a plurality of such windows, and so forth.

Unless otherwise indicated, all numbers expressing quantities of elements, dimensions such as width and area, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of a dimension, area, percentage, etc., is meant to encompass variations of in some embodiments plus or minus 20%, in some embodiments plus or minus 10%, in some embodiments plus or minus 5%, in some embodiments plus or minus 1%, in some embodiments plus or minus 0.5%, and in some embodiments plus or minus 0.1% from the specified amount, as such variations are appropriate to perform the disclosed methods or employ the disclosed compositions.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter. With respect to the terms "comprising", "consisting of", and "consisting essentially of", where one of these three terms is used herein, the presently disclosed and claimed subject matter can include the use of either of the other two terms.

As used herein, the term "and/or" when used in the context of a listing of entities, refers to the entities being present singly or in combination. Thus, for example, the phrase "A, S, C, and/or O" includes A, S, C, and O individually, but also includes any and all combinations and subcombinations of A, S, C, and O.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. The foregoing disclosure and description are illustrative and explanatory thereof, and various changes in the details of the illustrated apparatus and construction and method of operation may be made without departing from the spirit in scope of the invention which is described by the following claims.

We claim:

1. A process for measuring the effective thickness of a boron coating on copper foil comprising the steps of:
   (1) removing a sample of the boron coated copper foil from a larger length coated substrate;
   (2) weighing the sample of boron coated copper foil;
   (3) contacting the sample of boron coated copper foil with an etching solution;
   (4) allowing the etching solution to dissolve the sample of boron coated copper foil;
   (5) diluting the etching solution;
   (6) determining the concentration of the material in the diluted etching solution utilizing inductively coupled plasma optical emission spectroscopy; and
   (7) calculating the effective thickness of the coating ($t_s$) using the equation:

$$t_s=[(1.3 \times C \times V_s \times d_f \times t_{cu} \times d_{cu}/M_t) \times 1/(1-1.3 \times C \times V_s \times d_f/M_t)]$$

where C=measured concentration from determining step
   $d_f$=sample dilution factor
   $V_s$=volume of diluted etching solution
   $t_{cu}$=thickness of the copper foil
   $d_{cu}$—density of the copper foil
   $M_t$=mass of the boron coated sample.

2. The process of claim 1, wherein the removing a sample step comprises removing a sample at least about 1 square centimeter in size.

3. The process of claim 1, wherein the removing step comprises removing multiple samples from the substrate, the samples being taken at intervals of between about 50 and about 200 feet along the substrate.

4. The process of claim 1, wherein the boron coating comprises a boron carbide coating.

5. The process of claim 1 wherein the etching solution of the contacting step comprises a ceric ammonium nitrate solution.

6. The process of claim 5, wherein the ceric ammonium nitrate solution comprises between about 2 and about 25 percent by weight ceric ammonium nitrate.

7. The process of claim 5, wherein the ceric ammonium nitrate solution comprises between about 8 and about 10 percent by weight ceric ammonium nitrate.

8. The process of claim 1, wherein the diluting step comprises diluting the boron concentration to between about 2 and about 25 ppm.

9. The process of claim 1, wherein the determining the concentration step comprises determining the boron concentration to within about 0.1 ppm.

10. A process for measuring the effective thickness of a boron carbide coating on copper foil comprising the steps of:
    (1) removing a sample of the boron carbide coated copper foil from a larger length of boron carbide coated copper foil;
    (2) weighing the sample of boron carbide coated copper foil;
    (3) contacting the sample of boron carbide coated copper foil with ceric ammonium nitrate etching solution;
    (4) allowing the etching solution to dissolve the sample of boron carbide coated copper foil;
    (5) diluting the etching solution to between about 2 and about 25 ppm boron;
    (6) determining the concentration of boron carbide in the diluted etching solution using inductively coupled plasma optical emission spectroscopy; and
    (7) calculating the effective thickness of the boron coating ($t_s$) using the equation:

$$t_s=[(1.3 \times C \times V_s \times d_f \times t_{cu} \times d_{cu}/M_t) \times 1/(1-1.3 \times C \times V_s \times d_f/M_t)]$$

where C=measured concentration from determining step
   $d_f$=sample dilution factor
   $V_s$=volume of liquid sample prepared
   $t_{cu}$=thickness of the copper foil
   $d_{cu}$—density of the copper foil
   $M_t$=mass of the sample.

11. The process of claim 10, wherein the removing a sample step comprises removing a sample at least about 1 square centimeter in size.

12. The process of claim 10, wherein the removing step comprises removing multiple samples from the substrate, the samples being taken at intervals of between about 50 and about 200 feet along the substrate.

13. The process of claim 10, wherein the ceric ammonium nitrate solution comprises between about 2 and about 25 percent by weight ceric ammonium nitrate.

14. The process of claim 10, wherein the ceric ammonium nitrate solution comprises between about 8 and about 10 percent by weight ceric ammonium nitrate.

\* \* \* \* \*